(12) United States Patent
Barbut et al.

(10) Patent No.: US 6,217,552 B1
(45) Date of Patent: Apr. 17, 2001

(54) MEDICAL DEVICE FOR SELECTIVE INTRATHECAL SPINAL COOLING IN AORTIC SURGERY AND SPINAL TRAUMA

(75) Inventors: Denise R. Barbut; Mark-Hein Heinemann; Russel H. Patterson, all of New York, NY (US)

(73) Assignee: CoAxia, Inc., Maple Grove, MN (US)

( * ) Notice: Subject to any disclaimer, the term of this patent is extended or adjusted under 35 U.S.C. 154(b) by 0 days.

(21) Appl. No.: 09/287,969

(22) Filed: Apr. 7, 1999

Related U.S. Application Data

(63) Continuation-in-part of application No. 09/260,370, filed on Mar. 1, 1999, now abandoned.
(51) Int. Cl.$^7$ ........................................................ A61F 7/12
(52) U.S. Cl. ............................ 604/113; 607/113; 607/117
(58) Field of Search .................................. 604/27, 28, 500, 604/508, 113, 158, 164.01; 607/96, 113, 117

(56) References Cited

U.S. PATENT DOCUMENTS 4,781,672 * 11/1988 Hooven .
4,795,423 * 1/1989 Osterholm .
4,904,237 * 2/1990 Janese .
5,085,630 * 2/1992 Osterholm et al. .

\* cited by examiner

*Primary Examiner*—Anh-Tuan T. Nguyen
*Assistant Examiner*—Jeremy Thissell
(74) *Attorney, Agent, or Firm*—Lyon & Lyon LLP

(57) ABSTRACT

The invention provides a medical device having two elongate catheters, a pump, a refrigeration system, and a manometer. Each catheter has a proximal end, a distal end, a lumen therebetween and communicating with a distal port. The proximal ends of the catheters are connected to the pump and the refrigeration system. The distal ends are adapted for insertion into the subarachnoid space. The cerebral spinal fluid is aspirated from the first catheter to the pump, cooled to below body temperature, and returned to the second catheter. The flow rate of the cerebral spinal fluid is adjusted according the CSF pressure and temperature. Methods of using the devices in treating patients suffering from spinal trauma and undergoing aortic surgery are also disclosed.

19 Claims, 14 Drawing Sheets

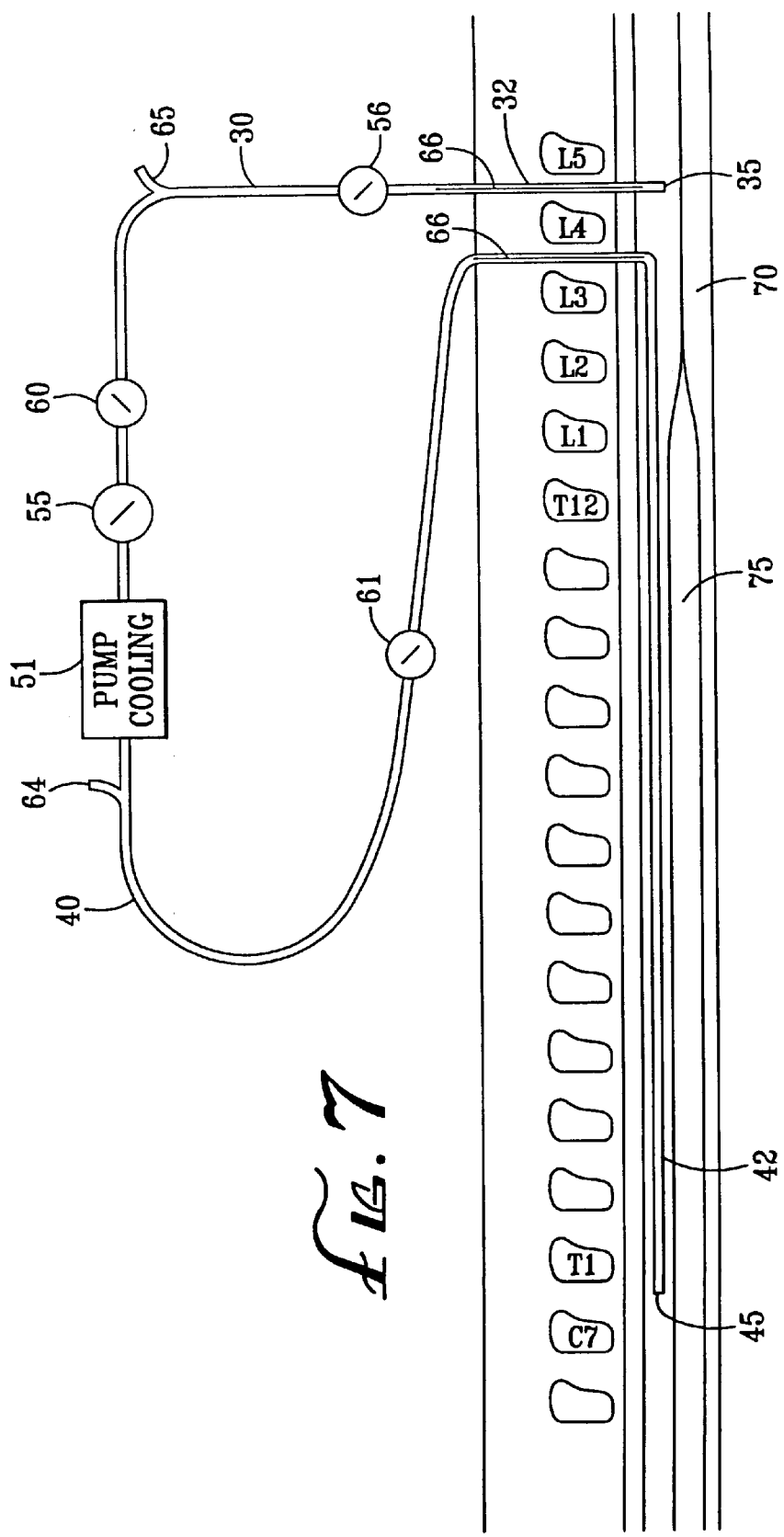

MEDICAL DEVICE FOR SELECTIVE INTRATHECAL SPINAL COOLING IN AORTIC SURGERY AND SPINAL TRAUMA

This is a continuation-in-part of U.S. application Ser. No. 09/260,370, filed Mar. 1, 1999, now abandoned the contents of which are expressly incorporated herein by reference.

FIELD OF THE INVENTION

The present invention generally relates to medical devices useful in reducing and preventing spinal injury in patients with spinal trauma or patients undergoing aortic surgery. More specifically, the invention provides devices for insertion into the subarachnoid space for circulating and cooling the cerebral spinal fluid below body temperature. The flow rate of the cerebral spinal fluid is variably adjusted according to the pressure and temperature, respectively measured by a manometer and thermometer.

BACKGROUND OF THE INVENTION

Spinal ischemia resulting in neurological complications occurs in patients sustaining a traumatic injury to the spinal cord or patients undergoing aortic surgery. Spinal cord injury can be classified as penetrating or blunt. In penetrating injuries, such as stab wound or gun shot wound to the spinal cord, complete severing of the spinal cord can occur, resulting in total muscular paralysis and loss of sensation below the level of injury. This condition of flaccid paralysis and suppression of all reflex activity following immediately upon transection of the spinal cord and involving all segments below the lesion is referred to as spinal shock. In most cases, reflex activity returns within 1 to 6 weeks from the onset of the spinal shock. Once transection of the spinal cord has occurred, peripheral reinnervation by the nervous system does not occur.

Spinal shock also occurs in blunt injuries, such as in motor vehicle accident, where compression of the spinal cord by impingement from fractured or dislocated vertebral bodies results in sensory and motor impairment below the level of cord involvement. Diagnosis of spinal fracture or dislocation is often made on X-rays. Spinal cord compression can be diagnosed on MRI, CT scan with myelogram, or lumbar puncture (Queckenstedt test). The mechanism of spinal ischemia is mostly caused by swelling of the cord. In these patients, hypotension may also occur as a result of loss of vascular sympathetic tone in the involved area. Urinary and/or bowel incontinence is a common complication due to impaired autonomic function.

Spinal ischemia is also a common postoperative complication following aortic surgeries, such as abdominal aortic aneurysmectomy. The incidence of spinal cord ischemia/stroke during aortic surgery is typically over 10%. During abdominal aortic aneurysm (AAA) repair, for example, the spinal arteries, which provide blood supply to the spinal cord, are often severed from the diseased aorta, and some but not all of which are later resutured to the prosthetic graft. As a result, blood flow to the spinal cord is reduced. When reduction of spinal perfusion lasts the duration of the surgery, typically more than forty-five minutes, spinal ischemia/stroke may ensue, often resulting in anterior spinal artery syndrome. The classic syndrome is characterized by paraplegia, rectal and urinary incontinence, loss of pain and temperature sensation, but with sparing of vibration and proprioceptive sense. Patients may also sustain neurologic deficits in the lower extremities after abdominal aortic surgery due to loss of posterior column modalities.

Brain damage associated with either stroke or head trauma is worsened by hyperthermia and improved with hypothermia. Current treatment for acute ischemic stroke and head injury is mainly supportive. A thrombolytic agent, e.g., tissue plasminogen activator (t-PA), can be administered to stroke patients who have no contraindication to t-PA. Current treatment for patients suffering from spinal injury is also supportive, e.g., to secure local hemostasis and to prevent infection by appropriate debridement, closure, and administration of antibiotics in penetrating spinal injury. In patients suffering from blunt injuries, surgical decompression of the spinal cord may be performed to restore neurological function. Spinal ischemia/stroke due to aortic surgery is also treated with supportive therapy, e.g., maintaining hemodynamic stability and monitoring neurological status, while waiting for the neurological deficits to recover with time. Therefore, besides surgical intervention in blunt injury, there is currently no good treatment which reduces neurologic damage to the spinal cord.

New devices and methods are thus needed in treating spinal ischemia/stroke in patients having spinal cord trauma or aortic surgery, in preventing spinal ischemia in patients anticipating a major thoracoabdominal surgery, or in cerebral ischemia, which minimizes neurological complication and improves the patients' quality of life without causing significant side effects.

SUMMARY OF THE INVENTION

The invention provides devices and methods for reducing neurologic complications in patients sustaining trauma to the spinal cord or undergoing aortic surgery. More specifically, the invention provides devices and methods for cooling the cerebral spinal fluid (CSF) surrounding the spinal cord.

A first embodiment of the device comprises two elongate catheters, each having a proximal end, a distal end, and a lumen communicating with a port at the distal end. The distal ends of the first catheter and the second catheter are adapted for insertion into a patient's subarachnoid space. The proximal ends of the catheters are connected to a pump to facilitate circulation of the CSF through the lumens of the catheters. A refrigeration system is connected to the pump to provide adjustable cooling of the CSF, such that CSF flowing through the lumen of the first catheter is cooled to below body temperature before flowing into the lumen of the second catheter. The CSF pressure in the circuit is measured by a manometer included in the catheters, the pump, or the refrigeration system. It will be understood that although the pump is advantageous, it may not be included in all embodiments for circulation of the CSF.

In another embodiment, the distal end of each catheter carries a needle which facilitates introduction of the devices into the subarachnoid space. A suture flange is mounted on a distal region of the first catheter and/or the second catheter for securing the devices after insertion into the subarachnoid space. Other embodiments of the devices include radiopaque markers mounted at the distal end of each catheter for identifying the position of the catheters in the subarachnoid space.

In still another embodiment, the proximal end of each catheter includes a port for infusing fluid, such as Ringer's lactate solution, or pharmaceutical agents into the subarachnoid space. The port can be used to drain the CSF for reducing pressure in the subarachnoid space. Alternatively, a release valve may be included proximally in one of the catheters to drain the CSF when the pressure exceeds a desired threshold. A distal region of each catheter may be angled relative to the proximal end to facilitate entry and rostral advancement in the subarachnoid space.

In still another embodiment, the devices include at least one thermometer. The thermometer can be included in the proximal end of the first and/or second catheter for measuring the temperature of the CSF or CSF/fluid mixture entering and exiting the subarachnoid space.

The methods for cooling the spinal cord to prevent neurologic damage during inadequate spinal perfusion utilize the devices disclosed herein. In a first method, the distal end of the first catheter is inserted percutaneously between the spinous processes of lumbar vertebrae L3 and L4 or L4 and L5 into the subarachnoid space. The distal end of the second catheter is inserted in the lumbar region at a level above or below the insertion of the first catheter. The second catheter is advanced rostrally in the subarachnoid space so that the distal port is positioned preferably in the low cervical or high thoracic region of the spine or optionally in the lumbar region. The position of the catheters can be verified under fluoroscopy in the embodiments where the distal ends of the catheters include one or more radiopaque marker. Preferably, the CSF is aspirated from the first catheter, cooled by the refrigeration system, and passed into the second catheter. Alternatively, the CSF is aspirated from the second catheter, cooled by the refrigeration system, and passed into the first catheter. In this manner, the CSF is cooled to below normal body temperature, which can be monitored by thermometers included in either or both catheters. The greater the cooling the greater the degree of protection is likely for the spinal cord.

In another method, after insertion of the catheters, the CSF is drained in the lumbar region to reduce the CSF pressure to zero. The CSF pressure can be monitored by a manometer included in either or both catheters. The CSF is collected in a bag and discarded after the procedure. Fluid, such as Ringer's lactate, is infused through one of the catheters, preferably the second catheter, and drained passively through the first catheter. The CSF collected in a bag may be discarded or reintroduced at the end of the procedure. The CSF/Ringer's lactate mixture is cooled through the refrigeration system and circulated by activating the pump. The pump can be either volume limited or pressure limited. The temperature of the CSF mixture can be reduced rapidly, and the flow rate is adjusted to maintain the desired temperature. The CSF pressure is maintained preferably at a minimum, i.e., at approximately zero, to maximize perfusion to the spinal cord.

In still another embodiment, a port protecting mechanism, e.g., a net or a fence guard, is mounted at the distal ends of the catheters. When the pump is activated, the mechanism prevents the arachnoid from folding over and obstructing the suction and port, and prevents nerve roots from being sucked into the catheter. The mechanism may be an integral part of the catheter, or be operably mounted on the inner catheter wall and deployed when the needle is withdrawn.

In still another method, the distal end of the first catheter is inserted between the spinous processes of lumbar vertebrae L3 and L4 or L4 and L5 into the subarachnoid space. The distal end of the second catheter is inserted between the spinous processes of low cervical vertebrae or high thoracic vertebrae, e.g., between C-6 and C-7, between C-7 and T-1, or between T-1 and T-2, into the subarachnoid space. The CSF is aspirated preferably through the first catheter, cooled through the refrigeration system to below body temperature, and passed into the second catheter. Alternatively, the CSF is aspirated from the second catheter in the low cervical or high thoracic region and passed into the first catheter in the lumbar region to provide spinal cooling. This method may be desirable in situations where the second catheter can not be advanced rostrally in the subarachnoid space due to an edematous spinal cord after injury.

It will be understood that although the devices and methods are most useful in treating patients with spinal trauma or undergoing aortic surgery, they can be utilized to reduce neurologic damage during cerebral hypoperfusion in situations, such as cardiac arrest, cardiac failure, low cardiac output states, stroke, head injury, cerebral aneurysm surgery, open and closed cardiac surgery and aortic surgery. Selective cooling of the cerebral tissues is preferred over systemic cooling, which may have undesirable effects on the heart and other organs and induce systemic coagulopathy. In using the devices, the distal end of the first catheter is inserted between the low cervical vertebrae or high thoracic vertebrae into the subarachnoid space. The distal end of the second catheter is inserted either in the lumbar region as described above or between the cervical vertebrae, in the foramen magnum, or through a skull burr hole into the subarachnoid space or the lateral ventricle. The CSF is preferably aspirated from the first catheter in the cervical subarachnoid space, cooled to below body temperature, and passed through the second catheter into the subarachnoid space in the cervical region or the brain. The patients may be tilted back and forth to improve circulation of the hypothermic CSF in patients with stroke, head trauma, or spinal injury. The flow rate of the CSF is adjusted according to the CSF temperature and pressure to maximize hypothermic protection on the cerebral tissues.

It will be understood that there are several advantages in using the devices and methods disclosed herein for reducing neurological complications which occur during aortic surgery or trauma. For example, the devices can be used (1) to provide continuous and variable spinal cooling, (2) in patients with either blunt or penetrating spinal trauma immediately after injury, (3) to selectively provide protective hypothermia to the spinal cord, thereby avoiding complications associated with systemic cooling, (4) by an anesthesiologist prior to aortic surgery, (5) to reduce neurologic deficits during cerebral hypoperfusion in patients with, e.g., stroke, cardiac failure, or cardiac surgery, (6) during aortic surgery, such as AAA repair, to lengthen the window for reattachment of the spinal arteries, and (7) to provide intrathecal administration of neuroprotective agents.

BRIEF DESCRIPTION OF THE DRAWINGS

FIG. 7 depicts the catheters of the device of FIG. 4 inserted in the lumbar region.

DETAILED DESCRIPTION

Figure 1:
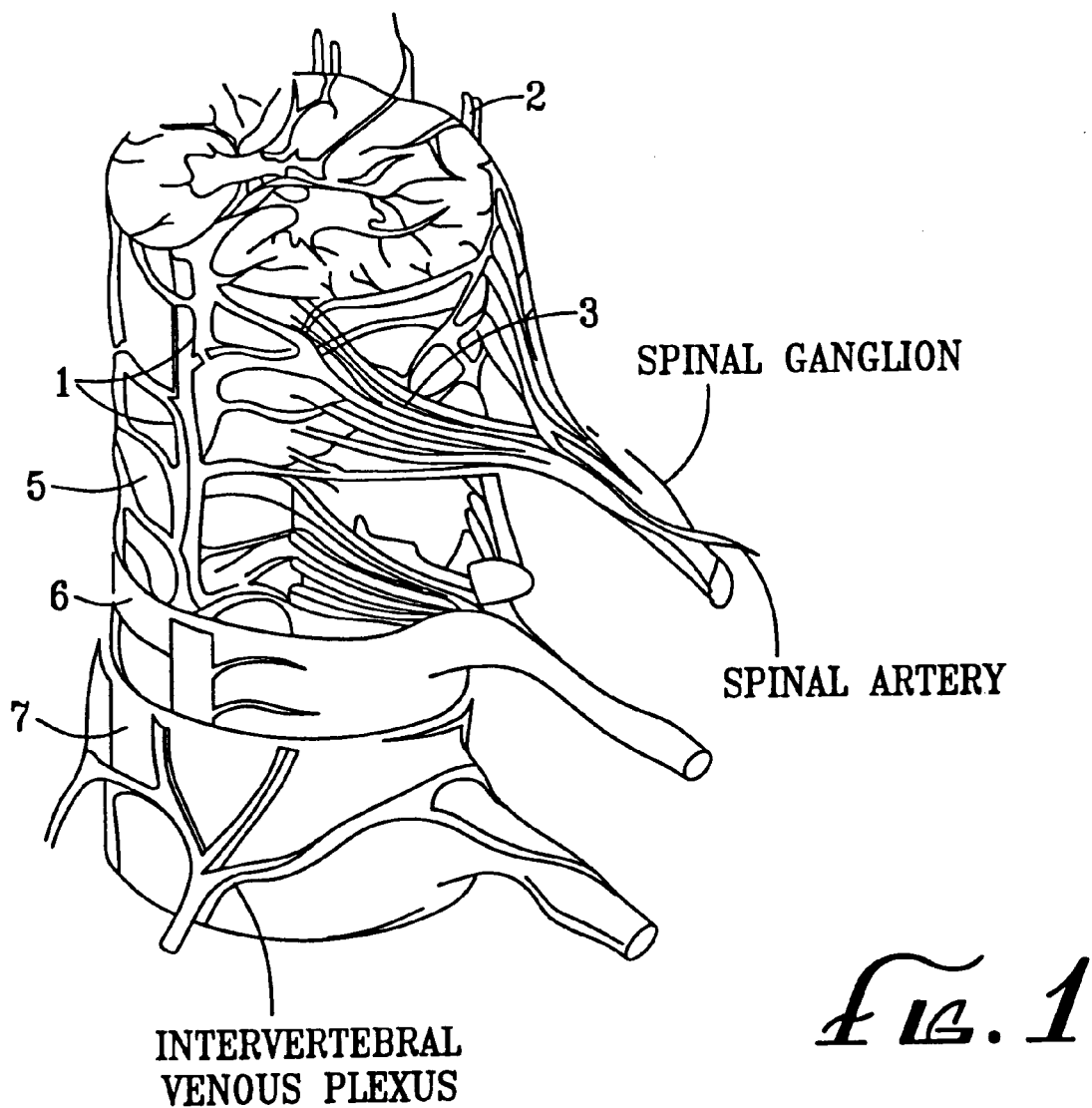
FIG. 1 depicts blood supply and venous drainage of the spinal cord.

The spinal cord, part of the central nervous system, is located in the vertebral canal (neural canal) which contains the spinal cord, its protective membranes, called spinal meninges, and associated vessels embedded in loose connective and fatty tissue. The spinal meninges include pia mater 5, arachnoid mater 6, and dura mater 7 as depicted in FIG. 1. The subaraclinoid space is formed between the pia mater and arachnoid mater. The epidural (extradural) space is formed between the arachnoid mater and the dura mater. During lumbar puncture, for example, the spinal needle is inserted into the lumbar interspinous space, and penetrates the dura mater and arachnoid mater to reach the subarachnoid space.

The spinal cord is supplied by three longitudinal arteries, i.e., an anterior spinal artery and two posterior spinal arteries, which are reinforced by segmental vessels called radicular arteries. These vessels are derived from branches of the vertebral, deep cervical, intercostal, and lumbar arteries, all of which branch from the aorta. In FIG. 1, anterior spinal artery 1, formed by two small branches from the vertebral arteries, supplies the anterior two-third of the spinal cord. Posterior spinal arteries 2, arise as small branches of either the vertebral or the posterior inferior cerebellar arteries, supply the posterior one-third of the spinal cord. Fracture and/or dislocations of the spinal column may interfere with blood supply to the spinal cord from the spinal arteries. The blood supply by the anterior and posterior spinal arteries is sufficient only for the superior cervical segments of the spinal cord. The remaining segments receive most of their blood supply from the radicular arteries, which supply the vertebrae, meninges, and the spinal arteries. Great anterior radicular artery 3 (also known as artery of Adamkiewicz) arises from an inferior intercostal or a superior lumbar artery. This artery is clinically important because it contributes to the anterior spinal artery, and therefore, when the intercostal or lumbar artery is severed, e.g., during aortic surgeries, the main blood supply to the inferior two-third of the spinal cord is compromised. These patients may lose all sensation and voluntary movement distal to the level of impaired blood supply to the spinal cord.

Figure 2:
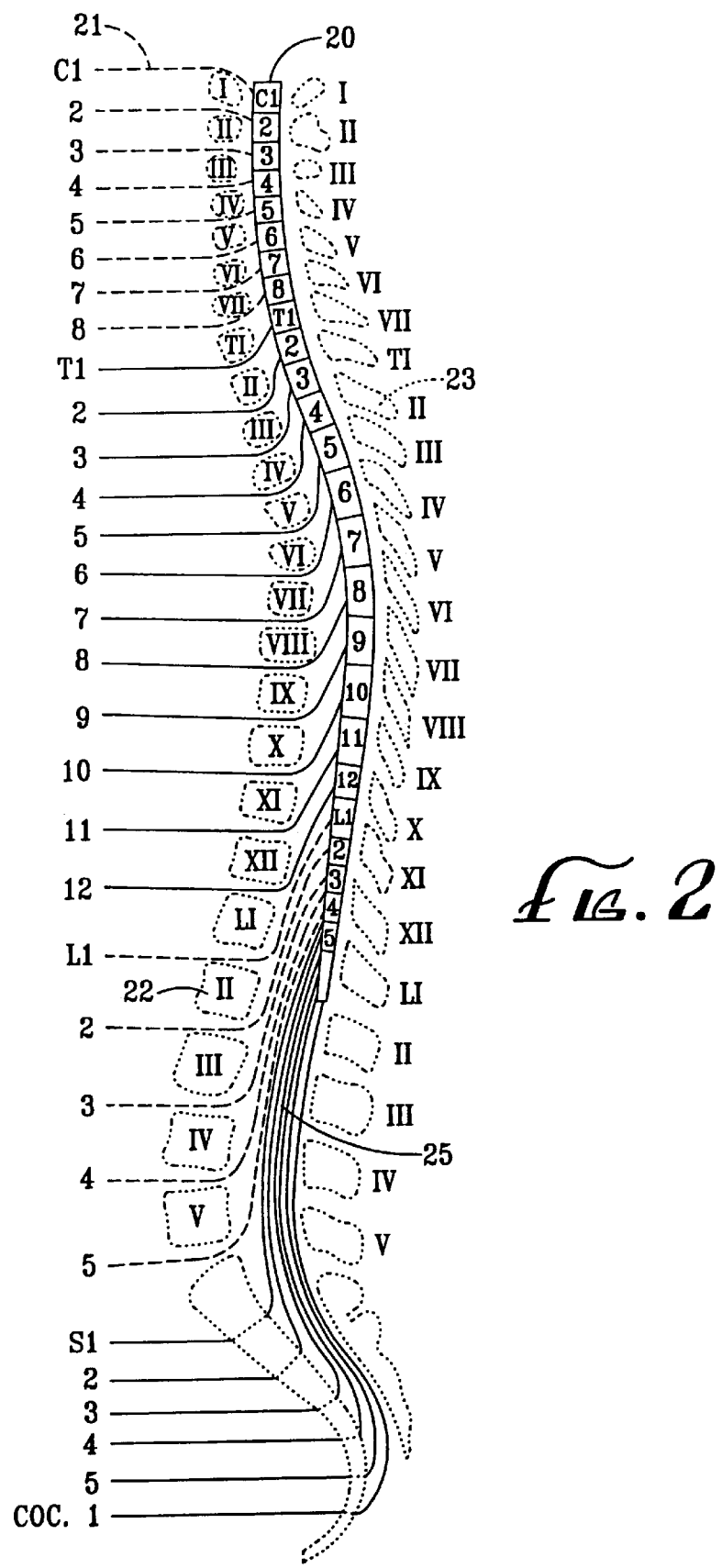
FIG. 2 depicts the relation of spinal cord segments to an adult patient's vertebral column.

The relation of spinal cord segments 20 to the adult vertebral column is illustrated in FIG. 2. The spinal cord lies in the spinal canal surrounded by vertebral bodies 22 anteriorly and spinous processes 23 posteriorly. The spinal cord begins as a continuation of the inferior part of the brain stem. In adults the spinal cord usually ends opposite the intervertebral disc between L1 and L2 vertebrae. There are 31 pairs of spinal nerves attached to the spinal cord by dorsal and ventral roots 21. The bundle of nerve roots in the subarachnoid space caudal to the termination of the spinal cord is cauda equina 25. The cerebral spinal fluid is usually obtained from the lumbar subarachnoid space between the spinous processes of L3 and L4 or L4 and L5 vertebrae because the spinal cord ends above these levels and is not likely to be damaged by a lumbar puncture needle or catheter.

Figure 3:
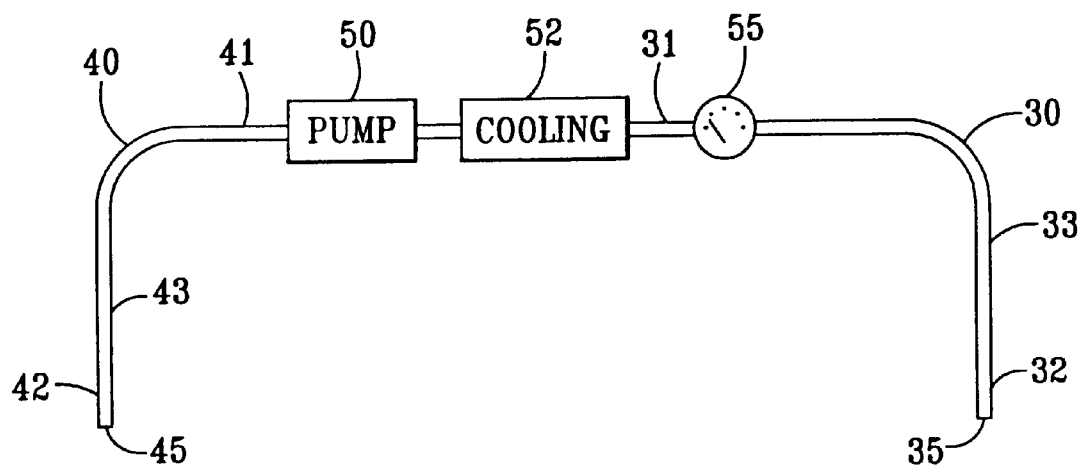
FIG. 3 depicts an embodiment of the medical device for providing spinal cord cooling according to the present invention.

FIG. 3 depicts a first embodiment of the device for cooling the spinal cord to prevent neurologic damage during inadequate spinal perfusion. The device includes two elongate catheters. First catheter 30 has lumen 33, proximal end 31, and distal end 32. The lumen communicates with port 35 at the distal end. Second catheter 40 has lumen 43, proximal end 41, and distal end 42. Lumen 43 communicates with port 45 at the distal end. Distal ends 32 and 42 are adapted for attachment to a lumbar puncture needle. Pump 50 is connected to proximal end 31 and 41 of the respective first and second catheters. Cooling system 52 is connected to pump 50 to provide variable cooling of the CSF. Proximal end 31 of the first catheter also includes manometer 55 for measuring CSF pressure in the circuit.

Figure 4:
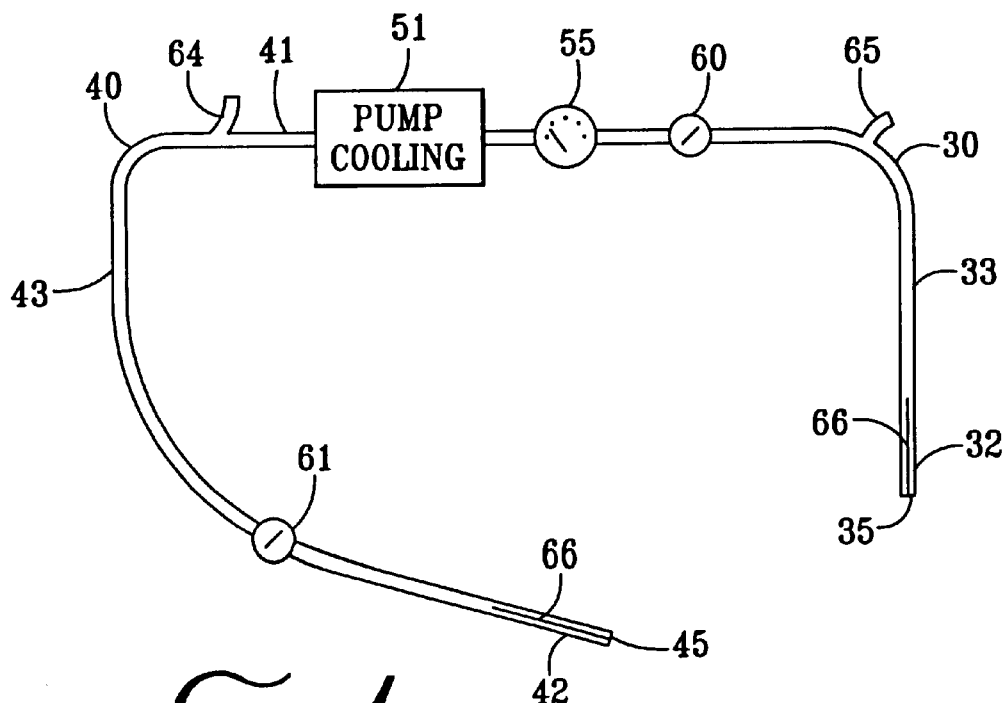
FIG. 4 depicts another embodiment of the medical device for providing spinal cord cooling according to the present invention.

FIG. 4 depicts another embodiment of the spinal cooling device. The device includes first and second catheter 30 and 40, each having, respectively, proximal end 31 and 41, distal end 32 and 42, and lumen 33 and 43. The proximal ends of the catheters are connected to pump and cooling unit 51, capable of providing circulation and cooling of the CSF in the circuit. The proximal end of the first catheter also includes manometer 55 and thermometer 60 for measuring, respectively, CSF pressure and temperature exiting or entering the first catheter. The proximal end of the second catheter also includes second thermometer 61 for measuring CSF temperature exiting or entering the second catheter. When the CSF pressure exceeds a desired threshold, the CSF can be drained from release valve 65 included in the first catheter or port 64 included in the second catheter. Port 64 can also be used to administer fluid or pharmaceutical agents into the subarachnoid space. Each distal end of the catheters carries needle 66, which facilitates introduction of the catheter into the subarachnoid space.

Figure 5A:
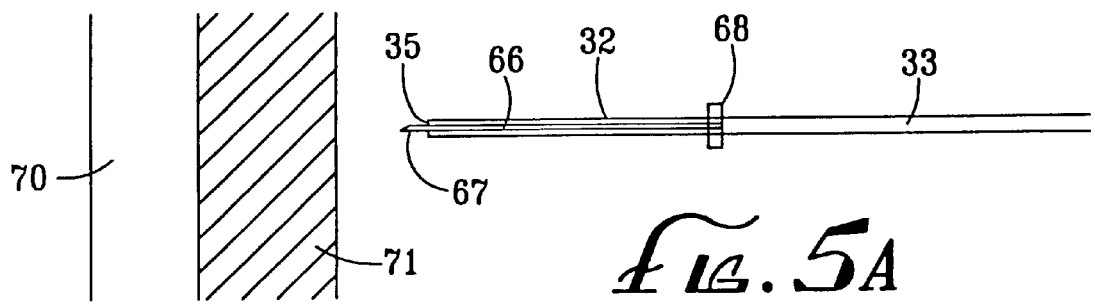
FIG. 5A depicts a distal end of another embodiment of the device including a needle.
Figure 5B:
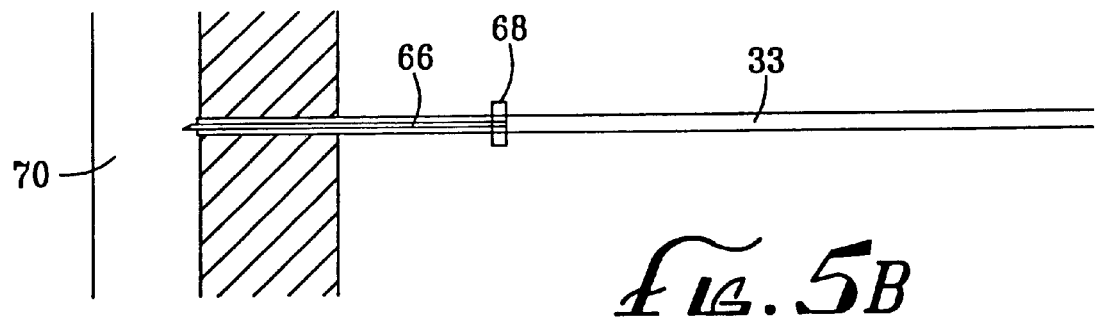
FIG. 5B depicts the distal end of the needle of FIG. 5A entering the subarachnoid space.
Figure 5C:
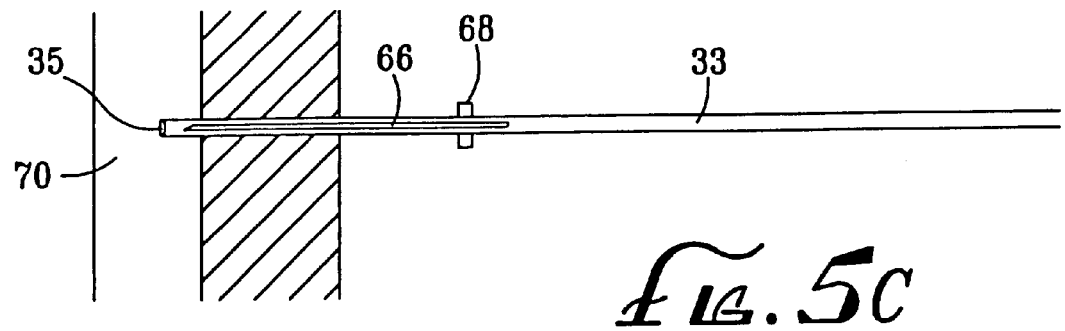
FIG. 5C depicts the distal end of the device of FIG. 5A entering the subarachnoid space.

FIGS. 5A, 5B, and 5C depict distal ends of an embodiment of the device carrying a needle. In FIG. 5A, needle 66 is carried in lumen 33 of distal end 32 of the catheter. Distal end 67 of the needle protrudes distally from port 35. The needle is movable within the lumen of the catheter by operating mechanism 68, capable of reversibly locking and releasing the needle in the lumen.

In use, distal end 67 of the needle is inserted through soft tissue 71 between the spinous processes of two vertebrae into subarachnoid space 70 as depicted in FIG. 5B. Once the entry of the subarachnoid space is confirmed by the backflow of the CSF through the needle into lumen 33, mechanism 68 is operated to release the needle in the lumen. Distal end 32 of the catheter is advanced distally over the needle to insert in the subarachnoid space as depicted in FIG. 5C. The CSF is then circulated through port 35 and lumen 33 of the catheter.

Figure 6A:
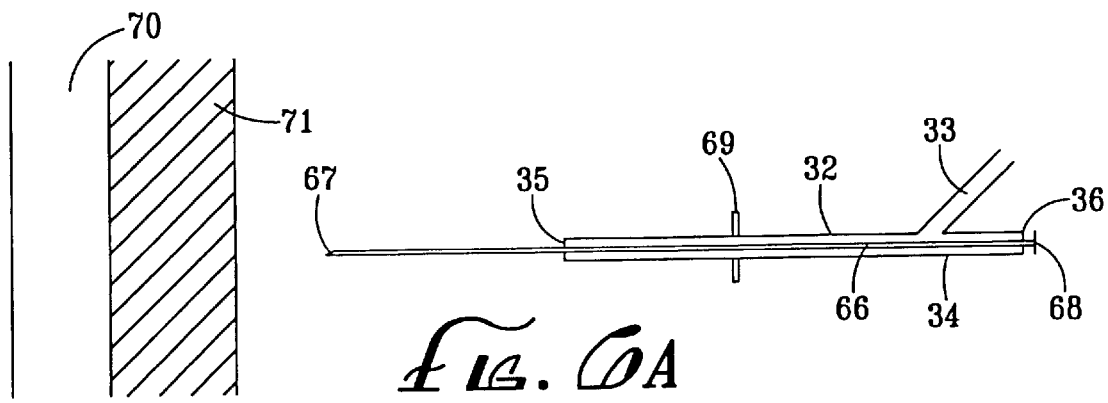
FIG. 6A depicts another embodiment of the needle carried at the distal end of a catheter.

Another embodiment of the catheter carrying a needle at its distal end is depicted in FIGS. 6A, 6B, 6C, 6D, and 6E. In FIG. 6A, distal end 32 of the catheter includes second lumen 34 for housing needle 66. Lumen 34 communicates with lumen 33 of the catheter, distally with port 35, and proximally with port 36. Needle 66, which has distal end 67 and proximal end 68, is slidably movable in lumen 34. Distal end 67 protrudes distally from port 35, and proximal end 68 protrudes proximally from port 36. Suture flange 69 is slidably mounted on distal end 32 of the catheter.

Figure 6B:
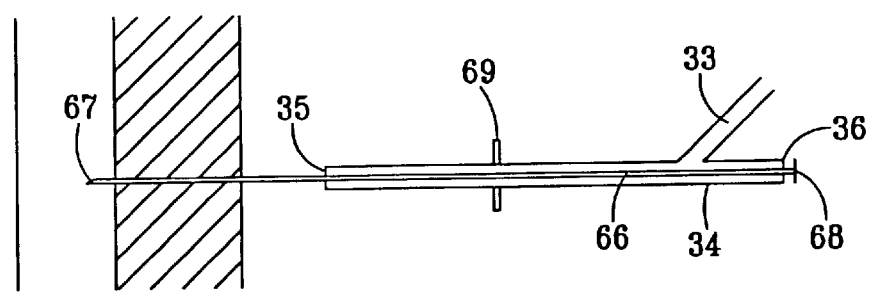
FIG. 6B depicts the needle of FIG. 6A inserted in the subaraclnoid space.
Figure 6C:
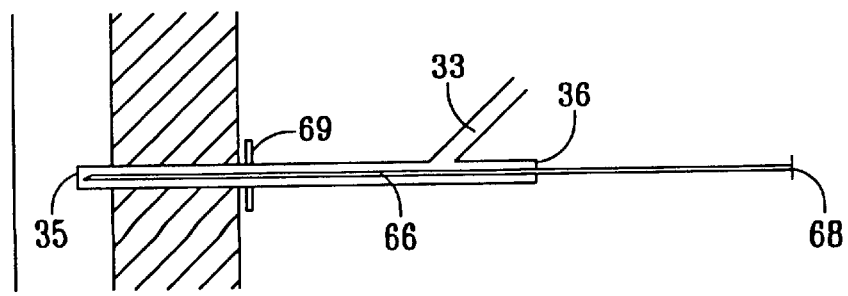
FIG. 6C depicts the needle and the distal end of the catheter of FIG. 6A inserted in the subarachnoid space.
Figure 6D:
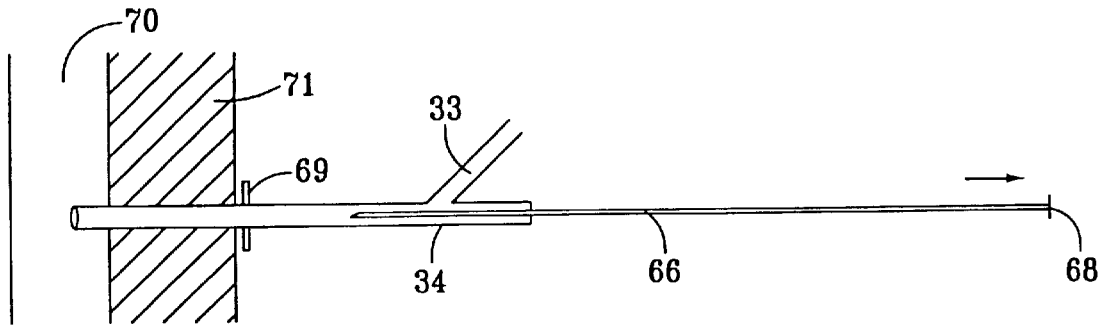
FIG. 6D depicts the needle of FIG. 6A being removed from the catheter.
Figure 6E:
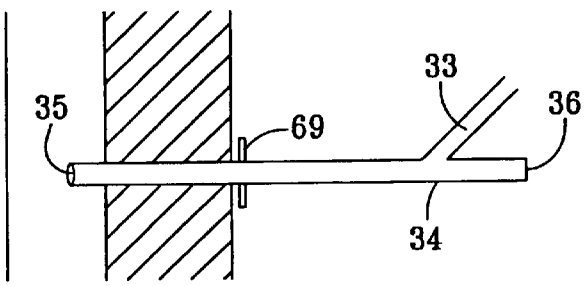
FIG. 6E depicts the device of FIG. 6A inserted in the subarachnoid space without the needle.

In use, distal end 67 of the needle is inserted through soft tissue 71 between spinous processes of two vertebrae into subarachnoid space 70 as depicted in FIG. 6B. While holding proximal end 68 of the needle, the distal end of the catheter is advanced distally over the needle to insert in the subarachnoid space as depicted in FIG. 6C. Needle 66 is removed from subarachnoid space 70 by pulling on end 68 proximally as depicted in FIG. 6D. Sutures can be placed between suture flange 69 and soft tissue 71 to secure the catheter. The needle can remain in lumen 34 or be removed completely from lumen 34. In FIG. 6E, after removal of the needle, the CSF is circulated through port 35 and lumen 33. Port 36 can also be used as a release valve for draining the CSF when the CSF pressure exceeds a desired threshold or as an infusion port for administering fluid, such as Ringer's lactate solution, or pharmaceutical agents into the subarachnoid space.

The devices disclosed herein are useful in reducing neurologic injury to the spinal cord following spinal trauma or aortic surgery by providing cooling of the CSF surrounding the spinal cord. In FIG. 7, the device of FIG. 4 is shown inserted in a patient's lumbar region. Under sterile condition, two lumbar punctures are performed. Needle 66, preferably 14 Gauge, carried in distal end 32 of first catheter 30 is inserted between spinous processes 23 of L4 and L5 into subarachnoid space 70. Needle 66 carried in distal end 42 of second catheter 40 is inserted between the spinous processes of L3 and L4 into subarachnoid space 70. In alternative methods, the needle and catheter may be inserted between L5 and S1, L2 and L3, or L1 and L2. The catheters are advanced distally over the needle so that port 35 and 45 receive the CSF. Port 35 of the first catheter is positioned in the lumbar subarachnoid space, whereas distal end 42 of the second catheter is advanced rostrally in the subarachnoid space until it is positioned in the low cervical or high thoracic region. Port 45 is shown positioned between the spinous processes of C7 and T1. Radiopaque markers may be mounted on the distal ends of the catheters so that the position of the distal ends can be confirmed radiologically. Insertion of the two catheters in the lumbar region is preferred because spinal cord 75 usually terminates about L2, and damage to the spinal cord due to instrumentation is not likely. Prior to the aortic surgeries, such as abdominal aneurysm repair, the device may be inserted by an anesthesiologist, so that the surgeon would not be inconvenienced.

After the catheters are secured in the subarachnoid space, the CSF from the lumbar region may be drained through release valve 65 to reduce the CSF pressure to approximately zero, which is measured by second manometer 56, optionally included in the distal end of the catheter. The CSF is normally collected in a bag and may be discarded or reintroduced after the procedure. Large bore catheters, e.g., 3 or 4 French, may be used to rapidly drain the CSF (at approximately 100–150 cc in 3–4 minutes), thereby eliminating the need of using suction, which may cause the arachnoid to obstruct the distal ports or inadvertent damage by suction on a nerve root. Fluid, such as Ringer's lactate, is infused through the second catheter and drained passively through the first catheter. Preferably, this CSF and Ringer's lactate mixture is withdrawn from the first catheter in the lumbar region, cooled by pump and cooling unit 51, and passed into the second catheter in the low cervical /high thoracic region. Alternatively, the CSF is withdrawn from the second catheter and passed into the first catheter. Any cooling of the CSF is beneficial in protecting the spinal cord from ischemic injury. The greater the cooling, the greater the degree of protection. The temperature of the CSF exiting and entering the subarachnoid space in the lumbar region is measured by thermometers 60 and 61, respectively. Using this method, the CSF temperature can be reduced rapidly. The flow rate of the recirculated CSF mixture can be adjusted to keep the CSF temperature and pressure at a desired level. It is desirable to keep the CSF pressure at a minimum, at approximately zero, to maximize any remaining perfusion in the spinal cord after injury. The cooling of the spinal cord and/or can be maintained during and/or several hours after aortic surgery, and be maintained several hours following spinal cord trauma or stroke. At the end of the cooling period, the CSF temperature is allowed to rise slowly. The catheters are then removed from the lumbar region.

Figure 8:
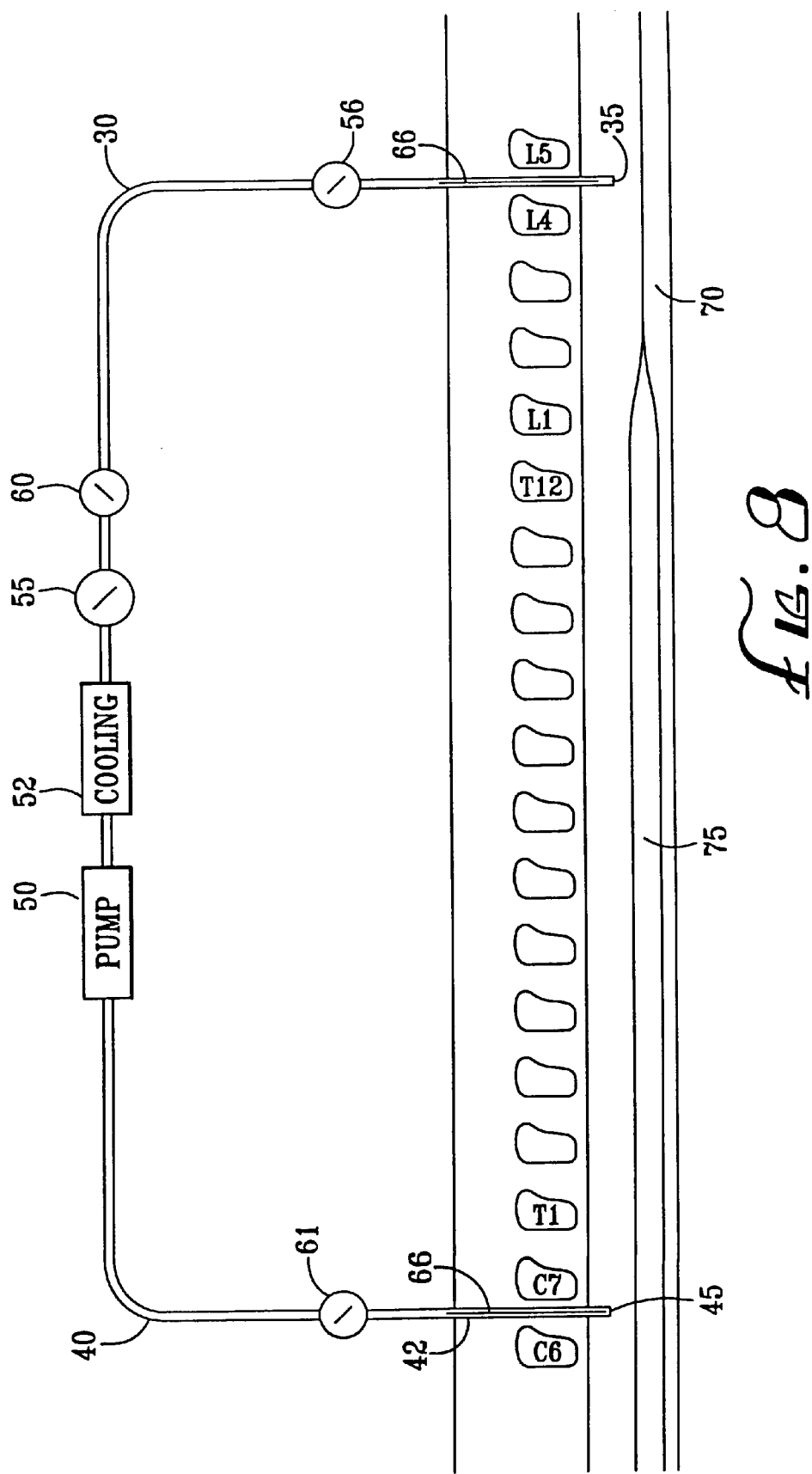
FIG. 8 depicts the catheters of another embodiment of the device inserted in the lumbar and cervical region.

Instead of having the second catheter inserted in the lumbar region, the second catheter can be inserted in the low cervical or high thoracic region. In FIG. 8, distal end 32 of first catheter 30 is inserted in the lumbar subarachnoid space between L4 and L5, whereas distal end 42 of second catheter 40 is inserted in the cervical subarachnoid space between C6 and C7. The distal ends of the catheters may be advanced over a needle into the subarachnoid space as described in FIGS. 5A, 5B, and 5C. This method may be preferred in situations where spinal cord 75 is very swollen and rostral advancement of the second catheter through the lumbar region is difficult. The second catheter may be inserted in the cervical region by a radiologist under fluoroscopy.

After the catheters are secured in the subarachnoid space, the CSF is aspirated through either catheter to the pump, cooled to below body temperature through a refrigeration system, and passed to the other catheter. Preferably, the CSF is aspirated from the first catheter in the lumbar region, and the cooled CSF or CSF/Ringer's lactate mixture is returned to the second catheter in the cervical region, closer to the site of spinal injury.

Figure 9:
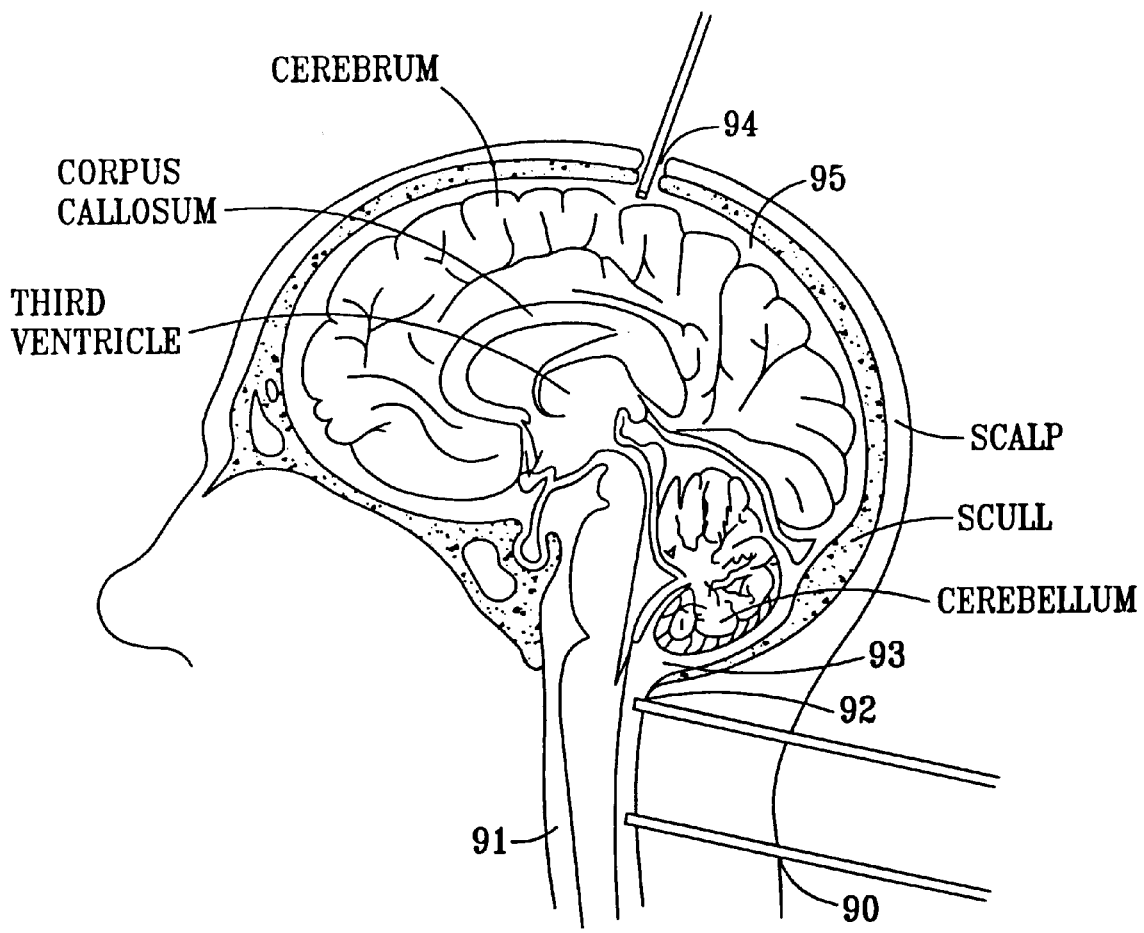
FIG. 9 depicts the device according to the present invention inserted in various cranial locations to provide cooling to the cerebral tissue.

Circulation of hypothermic CSF by inserting the distal ends of the first and second catheters in the spinal region may be sufficient to protect the brain in patients suffering from focal or hemispherical ischemia, since the spinal CSF communicates with the cerebral CSF. Alternatively, cooling of the cerebral CSF can be achieved by inserting the distal end of the first catheter between the spinous processes of two cervical vertebrae, and inserting the distal end of the second catheter in the cervical region 90 into spinal subarachnoid space 91, through foramen magnum 92 into cerebellomedullary cistern 93, or through skull burr hole 94 into the subarachnoid space 95 as depicted in FIG. 9. Alternatively, the second catheter can be inserted through a burr hole into the lateral ventricle (not shown). The CSF is preferably aspirated from the first catheter in the cervical region, cooled to below body temperature, and returned to the second catheter. The patient may be gently tilted back and forth to improve circulation of the CSF. This method is useful in situations where neurologic complications arise as a result of inadequate cerebral perfusion, such as cardiac arrest, cardiac failure, low cardiac output states, stroke, head injury, cerebral aneurysm surgery, open and closed cardiac surgery and aortic surgery. Selective cerebral cooling is advantageous over systemic cooling in that complications due to systemic cooling, such as cardiac arrhythmia, disseminated intravascular coagulopathy, and poor healing, can be avoided.

It will be understood that cooling of the brain and the spinal cord by intrathecal circulation of hypothermic CSF or CSF/Ringer's lactate mixture can be achieved by inserting the first catheter in the lumbar region and the second catheter in any spinal level or through skull burr hole in the ventricle. For example, intrathecal cooling of the cerebral tissue can be achieved by inserting the first catheter in the lumbar region and the second catheter one level immediately above or below the level of the first catheter insertion.

Figure 10A:
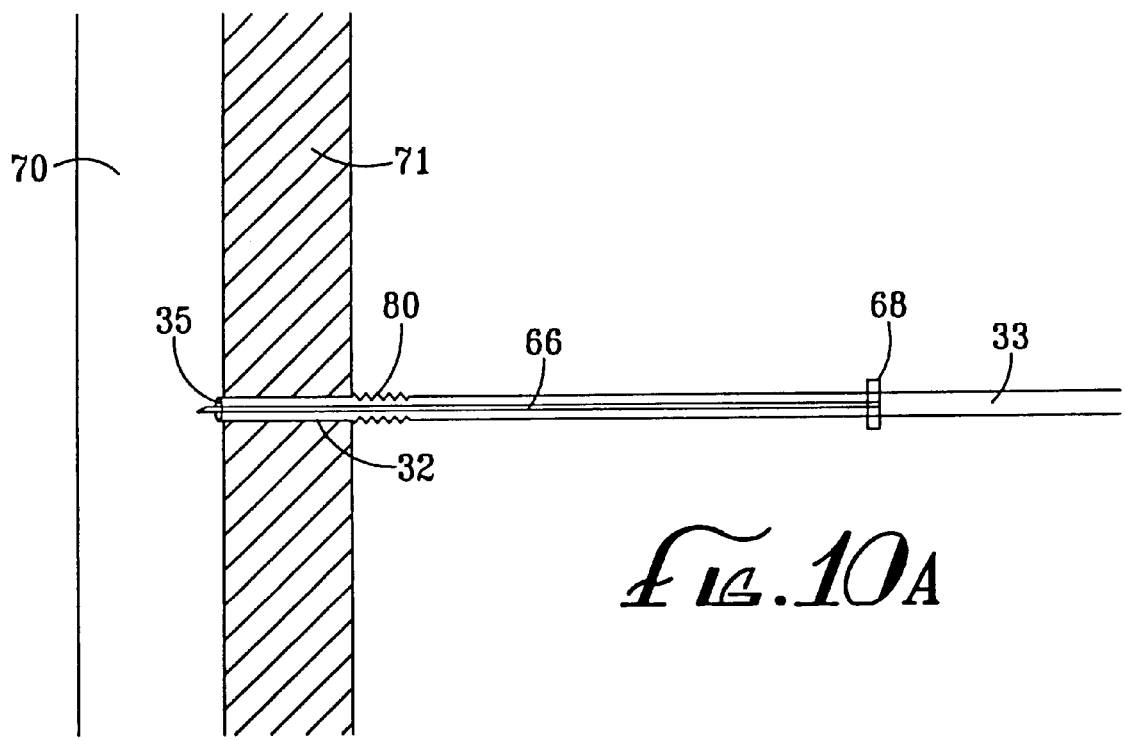
FIG. 10A depicts another embodiment of the catheter having a distal bendable region which assumes a linear configuration relative to the proximal end of the catheter.
Figure 10B:
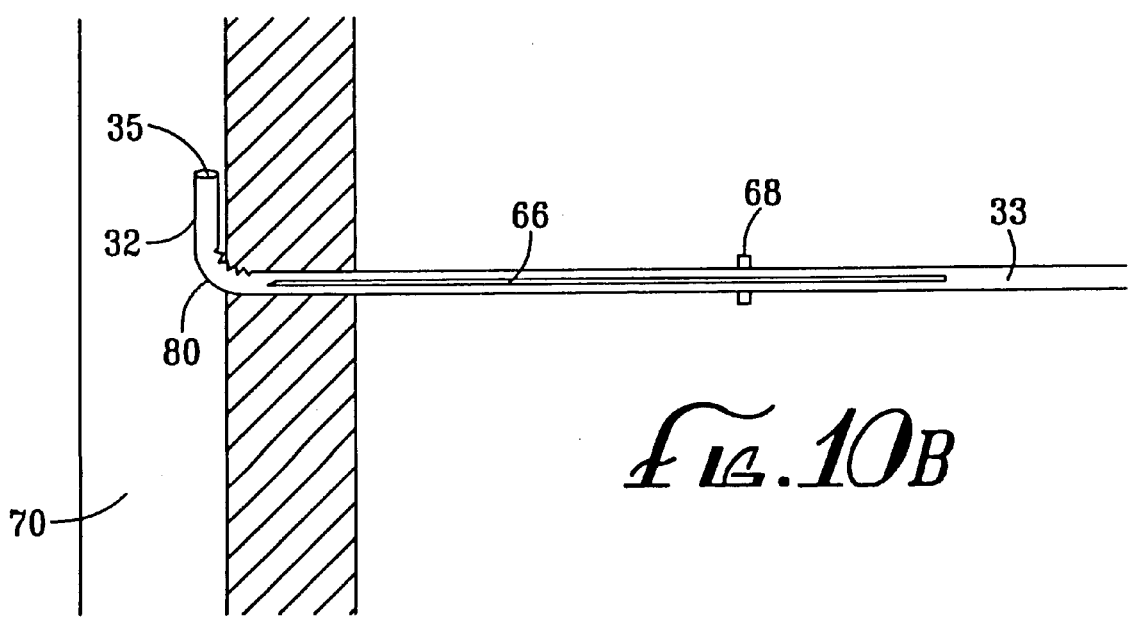
FIG. 10B depicts the catheter of FIG. 10A having the distal bendable region assuming an angled configuration relative to the proximal end of the catheter.

FIGS. 10A and 10B depict another embodiment of the catheter having bendable region 80 at distal region 32. In FIG. 10A, the distal end of the catheter is inserted through soft tissue 71 into subarachnoid space 70. As needle 66 is inserted through bendable region 80 and protrudes distal to port 35 into the subarachnoid space, distal region 32 assumes a linear configuration relative to the proximal end of the catheter. Once the entry of subaraclmoid space 70 is confirmed by the back-flow of the CSF through needle 66 into lumen 33, mechanism 68 is operated to release the needle in the lumen. Distal region 32 of the catheter is advanced distally over the needle to insert in the subarachnoid space as depicted in FIG. 10B. As bendable region 80 is advanced distally in the subarachnoid space over needle 66, distal region 32 assumes an angled configuration relative to the proximal end of the catheter. Distal port 35 can be positioned rostrally as shown in FIG. 10B or positioned caudally.

Figure 11A:
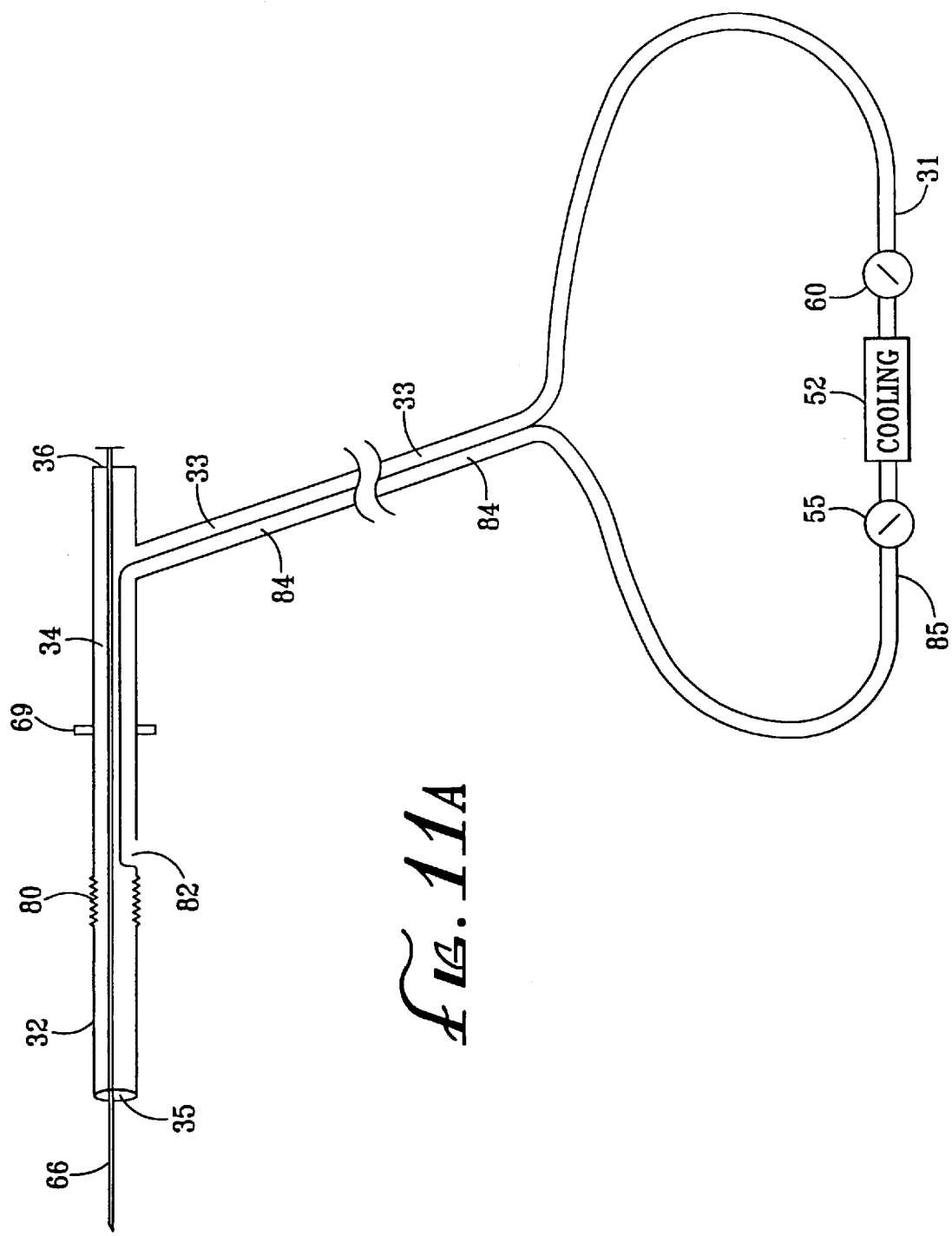
FIG. 11A depicts another embodiment of the catheter having a distal bendable region and a side port.
Figure 11B:
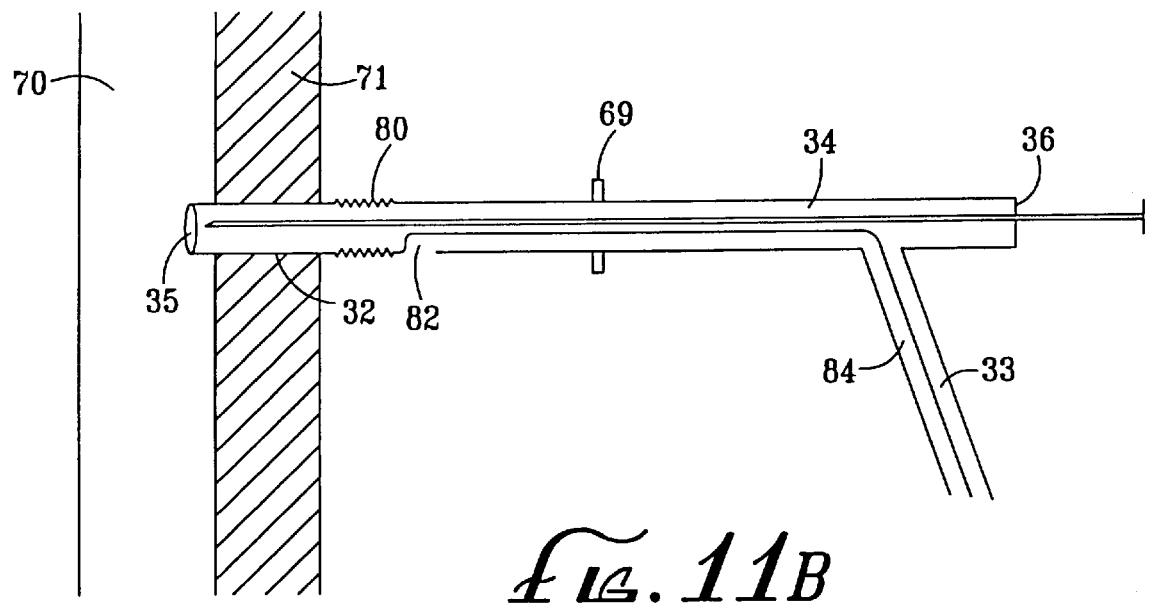
FIG. 11B depicts the catheter of FIG. 11A inserted in the subarachnoid space.
Figure 11C:
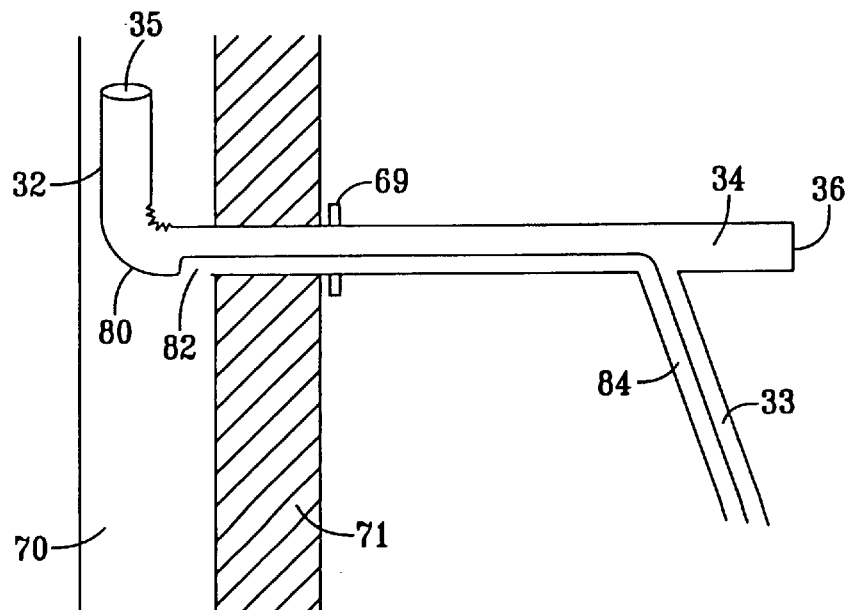
FIG. 11C depicts a distal region of the catheter of FIG. 11B assuming an angled configuration relative to the proximal end of the catheter.

FIGS. 11A, 11B, and 11C depict another embodiment of the device for intrathecal cooling of the CSF having bendable region 80 and side port 82 at distal region 32 of the catheter. In FIG. 11A the catheter has first lumen 33 and second lumen 84. The first lumen communicates with distal port 35, needle lumen 34, and proximal end 31, which includes thermometer 60 for measuring CSF temperature. The needle lumen communicates proximally with port 36, which can be used to drain CSF when the CSF pressure exceeds a desired threshold, or as an infusion port for administering fluid, such as Ringer's lactate solution, or pharmaceutical agents into the subarachnoid space. The second lumen communicates with side port 82 and proximal end 85, which includes manometer 55 for measuring CSF pressure. Cooling system 52 is connected to proximal ends 31 and 85 to provide variable cooling of the CSF. Slidable suture flange 69 is mounted on the catheter proximal to side port 82. Lumens 33 and 84 may be joined distally and separated proximally. Distal region 32 assumes a linear configuration relative to a proximal end of needle lumen 34.

In use, needle 66, which protrudes distal to port 35, is inserted in the subarachnoid space. Distal region 32 of the catheter, in a linear configuration with the proximal end of lumen 34, is advanced over the needle to insert in subarachnoid space 70 as shown in FIG. 11B. As bendable region 80 and side port 82 are advanced distally to position in subarachnoid space 70 as depicted in FIG. 11C, distal region 32 assumes an angled configuration relative to the proximal end of lumen 34 and distal port 35 is positioned rostrally in the subarachnoid space. Position of side port 82 is verified by back-flow of the CSF in lumen 84. The needle may be removed from lumen 34, leaving port 36 available to drain the CSF or infuse Ringer's lactate solution. Sutures can be placed on suture flange 69 to secure the catheter onto soft tissue 71. Preferably, the CSF is drained by gravity or by a pump from port 82, passed through lumen 84, cooled by the cooling system, and returned to port 35 through lumen 33 and 34. In this way, circulation of hypothermic CSF for protecting the brain and the spinal cord is achieved by inserting the device through a single spinal level, thereby eliminating the need for two spinal punctures.

Figure 12A:
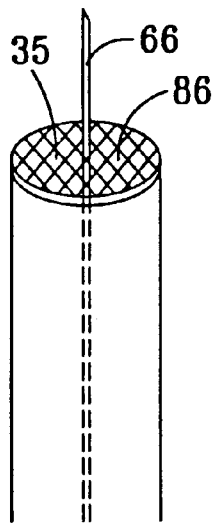
FIG. 12A depicts one embodiment of a port protecting mechanism having a net mounted over the distal port of the catheter.
Figure 12B:
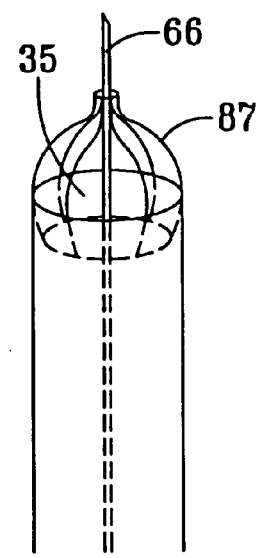
FIG. 12B depicts another embodiment of the port protecting mechanism having a fence guard mounted over the distal port of the catheter.
Figure 12C:
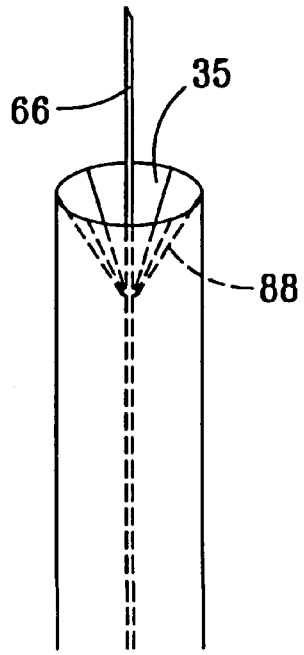
FIG. 12C depicts one embodiment of the port protecting mechanism mounted in the inner wall of the catheter.
Figure 12D:
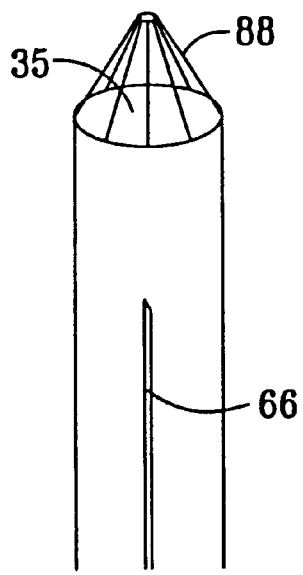
FIG. 12D depicts the port protecting mechanism of FIG. 12C after being activated by withdrawing the needle.
Figure 12E:
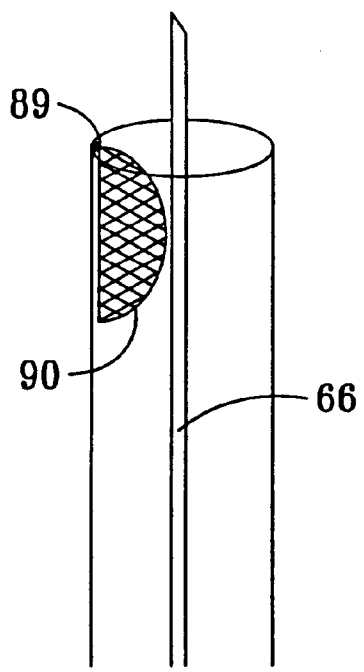
FIG. 12E depicts another embodiment of the port protecting mechanism having a moveable hinge mounted in the inner wall of the catheter.
Figure 12F:
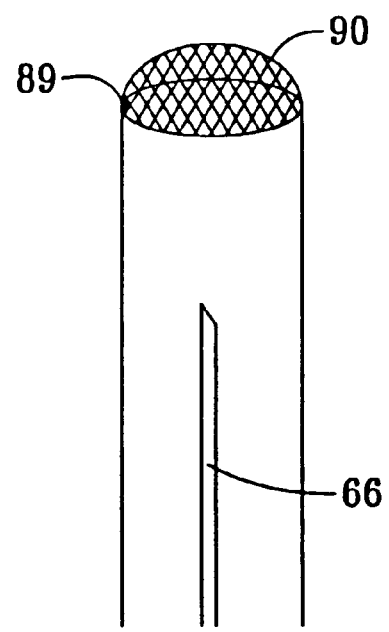
FIG. 12F depicts the port protecting mechanism of FIG. 12E covering the distal port of the catheter.

The distal end of the catheter may include a port protecting mechanism to protect the arachnoid from folding over or a nerve root from being sucked into the distal port of the catheter, especially when the pump is used. In FIG. 12A, net 86, which is mounted over port 35 at the distal end of the catheter, allows needle 66 to protrude distal to port 35 and prevents soft tissue from entering the port. In FIG. 12B, fence guard 87, another embodiment of the port protecting mechanism, is mounted at the distal end of the catheter. Needle 66 is inserted through the center of the fence guard. Both the fence guard and the needle protrude distal to port 35. In FIG. 12C, releasable protecting mechanism 88, operably associated with needle 66, is mounted in the inner wall of the distal end of the catheter. As needle 66 is withdrawn from distal port 35 as shown in FIG. 12D, protecting mechanism 88 is released distally overlying port 35, thereby preventing the arachnoid or a nerve root from entering the port during suction. In FIG. 12E, net 90, having a dome-like frame, is mounted on the distal end of the catheter by hinge 89. The hinge allows net 90 to open and close, thereby covering the distal port of the catheter. When net 90 is positioned adjacent the inner wall of the catheter, needle 66 is advanced distal to the open distal port, as depicted in FIG. 12E, for insertion of the catheter into the subarachnoid space. After needle 66 is withdrawn from the distal port, net 90 operates about hinge 89 to cover the distal port, as depicted in FIG. 12F, allowing the CSF, and not the arachnoid or nerve root, to enter the lumen of the catheter.

The length of the catheter will generally be between 20 to 100 centimeters, preferably approximately between 30 and 60 centimeters. The inner diameter of the catheter will generally be between 0.6 and 0.6 centimeters, preferably approximately 0.3 centimeters. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A method for cooling the spinal cord to prevent neurologic damage during inadequate spinal perfusion, comprising the steps of:

providing first and second elongate tubular members, each member having a lumen communicating with a port at a distal end;

inserting the first tubular member between lumbar vertebrae into the subarachnoid space;

inserting the second tubular member between lumbar vertebrae into the subarachnoid space, and advancing the distal port cephalad and locating the port in the cervical or thoracic region of the spine;

aspirating or draining cerebral spinal fluid (CSF) from the spinal column through one of the first tubular member or second tubular member;

cooling the CSF by extracorporeal refrigeration; and perfusing the CSF into the spinal column through the other of the first tubular member or second tubular member, wherein the spinal cord is cooled to below normal body temperature, and wherein CSF pressure is reduced to and maintained at a level substantially below normal CSF pressure.

2. The method of claim 1, wherein the first and second tubular members are inserted over a needle.

3. The method of claim 1, further comprising the step of measuring CSF pressure using a manometer.

4. The method of claim 1, further comprising the step of releasing CSF to reduce the pressure in the subarachnoid space.

5. The method of claim 1, further comprising the step of performing aortic surgery.

6. The method of claim 5, wherein the surgery is any one of thoracic and abdominal aortic aneurysm repair.

7. The method of claim 1, further comprising the step of mixing CSF with Ringer's lactate solution.

8. The method of claim 1, further comprising the step of adjusting the CSF flow rate.

9. The method of claim 1, further comprising the step of measuring CSF temperature.

10. The method of claim 1, further comprising the step of infusing fluid or neuroprotective agent into the subarachnoid space.

11. A method for cooling the spinal cord to prevent neurologic damage during inadequate spinal perfusion, comprising the steps of:

providing first and second elongate tubular members, each member having a lumen communicating with a port at a distal end;

inserting the first tubular member between lumbar vertebrae into the subarachnoid space;

inserting the second tubular member between low cervical vertebrae or high thoracic vertebrae into the subarachnoid space, and advancing the distal port cephalad and locating the port in the cervical, thoracic, or lumbar region of the spine;

aspirating cerebral spinal fluid (CSF) from the spinal column through one of the first tubular member or second tubular member;

cooling the CSF by extracorporeal refrigeration; and perfusing the CSF into the spinal column through the other of the first tubular member or second tubular member, wherein the spinal cord is cooled to below normal body temperature, and wherein CSF pressure is reduced to and maintained at a level substantially below normal CSF pressure.

12. The method of claim 11, wherein the first and second tubular members are inserted over a needle.

13. The method of claim 11, further comprising the step of measuring CSF pressure using a manometer.

14. The method of claim 11, further comprising the step of releasing CSF to reduce the pressure in the subarachnoid space.

15. The method of claim 11, further comprising the step of performing aortic surgery.

16. The method of claim 15, wherein the surgery is any one of thoracic and abdominal aortic aneurysm repair.

17. The method of claim 11, further comprising the step of infusing fluid into the subarachnoid space, and wherein the CSF is mixed with the fluid.

18. The method of claim 17, wherein the fluid is Ringer's lactate or saline solution.

19. The method of claim 11, further comprising the step of adjusting the CSF flow rate.

* * * * *